United States Patent [19]

Cohen et al.

[11] 4,007,258

[45] Feb. 8, 1977

[54] SUSTAINED RELEASE PESTICIDAL COMPOSITION

[75] Inventors: Arthur I. Cohen; James S. Y. Sim; Maurice H. Van Horn; Stanley E. Gordesky; Stanley I. Gordon, all of Rochester, N.Y.

[73] Assignee: Union Corporation, Verona, Pa.

[22] Filed: Sept. 10, 1973

[21] Appl. No.: 395,700

[52] U.S. Cl. .................... 424/22; 424/25; 424/36; 424/80; 424/81; 424/329; 424/359

[51] Int. Cl.² .......................................... A61K 9/26

[58] Field of Search ................ 424/19, 22, 25, 32, 424/33, 36, 81, 359, 329

[56] References Cited

UNITED STATES PATENTS

| | | | |
|---|---|---|---|
| 1,568,044 | 1/1926 | Bassett et al. | 424/359 X |
| 2,206,975 | 7/1940 | Ripper | 424/36 X |
| 2,846,353 | 8/1958 | Pipher | 424/359 X |
| 2,895,880 | 7/1959 | Rosenthal | 424/359 X |
| 3,116,206 | 12/1963 | Brynko et al. | 424/36 |
| 3,428,043 | 2/1969 | Shepherd | 128/268 |
| 3,435,117 | 3/1969 | Nichols | 424/359 X |
| 3,551,556 | 12/1970 | Kliment et al. | 424/21 |
| 3,566,874 | 3/1971 | Shepherd et al. | 128/349 |
| 3,577,516 | 5/1971 | Gould et al. | 424/16 |
| 3,628,974 | 12/1971 | Battista | 424/359 X |
| 3,641,237 | 2/1972 | Gould et al. | 424/16 |
| 3,660,071 | 5/1972 | Gould et al. | 71/65 |
| 3,674,901 | 7/1972 | Shepherd et al. | 424/27 |

*Primary Examiner*—Shep K. Rose
*Attorney, Agent, or Firm*—Pollock, Vande Sande & Priddy

[57] ABSTRACT

A sustained release pesticidal composition which includes a pesticide; a biological binding agent for the pesticide; and a matrix of a water-insoluble but water-swellable hydrophilic polymer.

6 Claims, No Drawings

SUSTAINED RELEASE PESTICIDAL COMPOSITION

BACKGROUND OF THE INVENTION

The present invention is concerned with a sustained release pesticidal composition,, and in particular is concerned with a sustained release pesticidal composition which contains a pesticide; a binding agent for the pesticide; and a matrix of a water-insoluble but water-swellable hydrophilic polymer. The present invention is also concerned with methods for preparing the pesticidal compositions.

It has previously been suggested to incorporate pesticides into hydrophilic polymers to provide sustained release of the pesticide. However, the particular pesticides which have to date been satisfactorily employed in such a sustained release mechanism are very limited since not every combination of a pesticide and any type of hydrophilic polymer provides a suitable slow release mechanism. Furthermore, such systems are not very susceptible to tailoring the release for a particular application. That is, the slowing down or speeding up of a release system is not readily accomplished. In addition, many prior suggested sustained release pesticidal compositions require relatively large quantities of synthetic materials.

Accordingly, it is an object of the present invention to make it possible to provide sustained release pesticidal compositions which are applicable for a large variety of pesticidal agents. Another object of the present invention is to provide a means by which it is possible to selectively alter the release characteristics for a particular application. A further object of the present invention is a reduction in the quantity of synthetic materials without a concomitant reduction in the release characteristics of the pesticidal compositions.

SUMMARY OF THE INVENTION

The present invention is concerned with a sustained release pesticidal composition comprising a pesticide in an amount at least sufficient for the total dosage requirement during a treatment period; a biological binding agent for the pesticide wherein the biological binding agent contains bonding sites complementary to bonding sites of the pesticide in an amount effective to bind the pesticide and to provide for the sustained release of the pesticide in the desired dosage amount; a matrix of a water-insoluble but water-swellable hydrophilic polymer which holds the biological binding agent; and the molecular size or weight of the biological binding agent is sufficient to cause retention of said biological binding agent in the matrix and to prevent egress of the biological binding agent from the matrix during the treatment period.

The present invention is also directed to a method of preparing the above-described sustained release pesticidal composition which comprises admixing a monomeric composition being polymerizable to form a water-insoluble but water-swellable hydrophilic polymer and the biological binding agent; polymerizing the monomeric mixture to form a matrix of a water-insoluble but water-swellable hydrophilic polymer having dispersed therein the biological binding agent; and then adding to the resultant product a pesticide in an amount at least sufficient for the total dosage requirement during the treatment period.

The present invention is also concerned with a process for preparing the sustained release pesticidal compositions as discussed above which comprises contacting the pesticide with the biological binding agent to bond the pesticide to the biological binding agent; admixing the resulting composition with a monomeric composition being polymerizable to a water-insoluble but water-swellable hydrophilic polymer; and polymerizing to provide the sustained release pesticide composition as defined hereinabove.

DESCRIPTION OF PREFERRED EMBODIMENTS

The pesticide employed according to the present invention can be any material suitable for controlling or destroying any pest (i.e., plant or animal) that is detrimental or annoying to man. Generally the molecular weight of the pesticide is less than about 10,000 and preferably less than about 5,000. Most of the pesticides have molecular weight of 1,000 or less. Some non-limiting examples of pesticides include herbicides, bactericides, fungicides, insecticides, miticides, antifoulants, and nematocides.

Some illustrations of herbicides include 2-(ethylamino)-4-(isopropylamino)-6-(methylthio)-s-triazine, 3-amino-2,5-dichlorobenzoic acid, 3-amino-1,2,4-triazole, ammonium sulfamate-2-trizine, 2-chloro-4-ethylamino-6-isopropylamino-s-triazine, polychlorobicyclopentadiene, 4chloro-2-butynyl-m-chlorocarbanitate, N-butyl-N-ethyl-$\alpha$, $\alpha$, $\alpha$, trifluoro-2,6-dinitro-p-toluidine, S-(O,O-diisopropyl phosphorodithioate) ester of N-(2-mercaptoethyl) benzenesulfamide, methyl m-hydroxycarbanilate, m-methyl carbonilate, 3,5-dibromo-4-hydroxybenzonitrile, S-ethyl diisobutylthiocarbamate, N,N-diallyl-2-chloroacetamide, 2-chloroallyl diethyldithiocarbamate, 3-[p-(pchlorophenoxy)phenyl] 1,1-dimethylurea, isopropyl m-chlorocarbanilate, calcium methanearsonate, p-chlorophenoxy acetic acid, S-ethyl N-ethyl-N-cyclohexylthiocarbamate, 3', 4'-dichlorocyclopropanecarboxanilide, 2,4-dichlorophenoxy acetic acid and its salts, e.g. butylamine salt, and esters, e.g. isooctyl ester, 2,4,5-trichlorphenoxy acetic acid and its salts and esters, 2,2-dichloropropionic acid, 4-(2,4-dichlorophenoxybutyric acid its salts, amine salts and esters, dimethyl-2,3,5,6-tetrachlorpphthalate, 1,3-bis(1-hydroxy-2,2,2-trichloroethyl) urea, tris[(2,4-dichlorophenoxy)ethyl] phosphite, S-2,3-dichloroallyl diisopropylthiocarbamate, 3,6-dichloro-o-anisic acid, 2,6-dichlorobenzo-nitrile, 2-(2,4-dichlorophenoxy) propionic acid, N,N-dimethyl-2,2-diphenylacetamide, diphenyl-acetonitrile, 3-(3,4-dichlorophenyl)-1,1-dimethylurea, 2-methyl-4,6-dinitrophenol sodium salt, disodium methanearsonate, ethylene glycol bis(trichloroacetate), 7-oxabicyclo (2,2,1) heptane-2,3-dicarboxylic acid, -S-ethyl dipropylthiocarbamate, 2-(2,4,5-trichlorophenoxy) ethyl 2,2-dichloropropionate, diethyl dithiobis(thionoformate), 2,3,6-trichlorophenylacetic acid or sodium salt, 3-phenyl-1,1-dimethylurea, 3-phenyl-1,1-dimethylurea richloroacetate, 1,1-dimethyl-3-($\alpha$, $\alpha$, $\alpha$-trifluoro-m-tolyl) urea, 2-t-butylamino-4-ethylamino-C-methylthio-s-triazine, 3,5-diiodo-4-hydroxybenzonitrile, hexachloroacetone, 5-bromo-3-sec-butyl-6methyluracil, potassium cyanate, 2-chloro-2', 6'-diethyl-N-(methoxymethyl) acetanilide, 3-cyclohexyl-6,7-dihydro-1H-cyclo-pentapyrimidine-2,4(3H, 5H)-dione, 3-(3,4-dichlorophenyl)-1-methoxy-1-methylurea, 3-(4-bromo-3-chlorophenyl)-1-methoxy-1-methylurea, mono ammonium methyl arsenate, 2-methyl-4-chlorophenoxyacetic acid and its salts and esters, 4-(2-methyl-4-chlorophenoxy) butyric acid and its salts and esters, 2-(2-methyl-4-chlorophenoxy) propionic acid and its salts and esters, 1,2-dihydro 3,6-pyridazinedione, S-ethyl hexahydro-1H-azepine-1-carbothioate, 3-(p-chlorophenyl)-1,1-dimethylurea, 3-(4-chlorophenyl)-1,1-dimethylurea trichloroacetate, 2,4-bis [(3-methoxypropyl)-amino]-6-methylthio-s-triazine, monosodium acid methanearsonate, N-1-naphthylphthalamic acid, 1-butyl-3-(3,4-dichlorophenyl)-1-methylurea, ethyl hydrogen 1-propyl phosphonate, 4-(methylsulfonyl)-2,6-dinitro-N,N-dipropylaniline, 2,4-dichlorophenyl-p-nitrophenyl ether, 3-(hexahydro-4,7-methanoinden-5-yl)-1,1-dimethylurea, 1,1'-dimethyl-4,4'-bipyridinium dichloride or the corresponding bis (methyl sulfate), dimethylamine salt of polychlorobenzoic acid (PBA), pentachlorophenol, S-propyl butylethylthiocarbamate, 4-amino-3,5,6-trichloropicotinic acid, 2,4'-dinitro-4-trifluoromethyldiphenyl ester, 2,4-bis(isopropylamino)-6methyl-thio)-s-triazine, 2-chloro-N-isopropylacetanilide, 3,4-dichloropropionanilide, 2-chloro-4,6-bis(isopropylamino)-s-triazine isopropyl N-phenylcarbamate, 5-amino-4-chloro-2-phenyl-3(2H)-pyridazinone, sodium 2-(2,4-dichlorophenoxy)-ethyl sulfate, 1-(2-methylcyclohexyl)-3-phenylurea, 2-(2,4,5-trichlorophenoxy) propionic acid and its salts and esters, 2-chloro-4,6-bis(ethylamino)-s-triazine, sodium arsenite, sodium chlorate, 3'-chloro-2-methyl-p-valerotoluidine, m-(3,3-dimethylureiodo)phenyl t-butyl carbamate, dimethylamine salt of 2,3,6-trichlorobenzoic acid, 2,3,6-trichlorobenzyloxypropanol, trichloroacetic acid, trichlorobenzyl chloride, 3-t-butyl-5-chloro-6-methyluracil, 2,6-di-t-butyl-p-tolylmethylcarbamate, S-2,3,3-trichloroallyl-diisopropyl thiolcarbamate, α, α, α-trifluoro-2,6-dinitro-N,N-dipropyl-p-toluidine and S-propyl dipropylthiolcarbamate.

Examples of some antifoulants are cuprous oxide, copper powder, mercuric oxide, cuprous oxide-mercuric oxide (e.g., 3:1 mercurous chloride), organotin compounds including triphenyltin chloride, triphenyltin bromide, tri-p-cresyltin chloride, triethyltin chloride, tributyltin chloride, phenyl diethyltin fluoride, tri(p-chlorophenyltin) chloride, tri(m-chlorophenyltin) chloride, dibutyl ethyltin bromide, dibutyloctyltin bromide, tricyclohexyltin chloride, triethyltin stearate, tributyltin stearate, triethyltin fluoroide, tributyltin fluoride, diphenyl ethyltin, chloride, diphenyl ethyltin fluoride, triphenyltin hydroxide, riphenyltin thiocyanate, triphenyltin richloroacetate, tributyltin acetate, tributyltin neodecanoate, tributyltin neopentanoate, trioctyltin neodecanoate, tributyltin oxide, trioctyltin oxide, triphenyltin fluoride, tripropyltin oleate, tripropyltin neodecanoate, tributyltin laurate, tributyltin octanoate, tributyltin dimethyl carbamate, tributyltin resinate, tributyltin chromate, amyldiethyltin neodecanoate, tributyltin naphthenate, tributyltin isooctylmercaptoacetate, bis-(tributyltin)oxalate, bis-(tributyltin) malonate, bis-(tributyltin) adipate, bis-(tributyltin) carbonate, organo lead compounds, e.g., triphenyl lead acetate, triphenyl lead stearate, triphenyl lead neodecanoate, triphenyl lead oleate, triphenyl lead chloride, triphenyl lead laurate, triethyl lead oleate, triethyl lead acetate, triethyl lead stearate, trimethyl lead stearate, triphenyl lead bromide, triphenyl lead fluoride, organic compounds including 10,10'-oxybisphenoxazine (SA-546), 1,2,3-trichloro-4,6-dinitrobenzene, hexachlorophene, dichlorodiphenyl trichloroethane (DDT), phenol mercuric acetate, tetrachloroisophthalonitrile, bis-(n-propylsulfonyl) ethylene.

Examples of bactericides include trimethyl benzyl ammonium chloride, cetyl pyridinium chloride, hexachlorophene, streptomycin, salicylic acid, penicillin aureomycin, chloromycetin, merthiolate, sulfanilamide, and sulfathiazole.

Exemplary of some fungicides are methyl-1-(butylcarbamoyl)-2-benz-imidazole carbamate, N-trichloromethylthio-4-cyclohexane 1,2-dicarboximide, methyl mercury, 2,3-dihydroxypropyl mercaptide, methyl mercury acetate, N-(ethylmercury)-p-toluenesulfonanilide, chloranil, 1,4-dichloro-2,5-dimethoxybenzene, copper carbonate, copper oleate, basic cupric chloride, cuprous oxides, 3-[2-(3,5-dimethyl-2-oxocyclohexyl)-2-hydroxy ethyl]glutarimide, 2,4,5,6-tetrachloroisophthalonitrile, tetrahydro-3,5-dimethyl-2H-3,5-thiadiazine-2-thione, 2,6-dichloro-4-nitroaniline, p-dimethylaminobenzenediazo sodium sulfonate bis(n-propylsulfonyl) ethylene (B-1843), 2,3-dichloro-1,4-napthoquinone, bis-N-[(1,1,2,2-tetrachloroethyl)-thio]-4-cyclohexene-1,2-dicarboximide, coordination product of zinc and manganese ethylene bisdithiocarbamate (Dithane M-45), mixture of nickel sulfate and manganous ethylene bis-[dithiocarbamate] (Dithane S-31), dodecylguanidine acetate, 2,4-dichloro-6-(o-chloroanilino)-s-triazine, sodium ethylmercurithiosalicylate, 3,4,5,6,7,7-hexachloro-N-(ethyl mercuri-1,2,3,6-tetrahydro-3,6-endomethanaphthalimide, ferric dimethyl dithiocarbamate, N-(trichloro-methylthio)phthalimide, 2-heptadecyl-imidazoline acetate, Griseofulvin, hexachlorobenzene, 1-chloro-2-nitropropane, manganous ethylene bis carbamate, 3,4,5,6,7,7-hexachloro-N-(methylmercuri)-1,2,3,6-tetrahydro-3,6-endo-methanophthalimide, mercuric chloride, sodium methyldithiocarbamate, 6-methyl-2,3-quinoxalinedithiol cyclic-S,S-dithiocarbonate, disodium ethylenebisdithiocarbamate, manganese dimethyl dithiocarbamate and mercaptobenzothiazole mixture, (Niacide), methyl mercury 8-hydroxyquinoline, 2-phenylphenol, methyl mercury dicyandiamide, phenylmercuritriethanolammonium lactate, pentachloronitro-benzene, phenylmercury urea, 3-(2-methylpiperidino) propyl 3,4-dichlorobenzoate, 2,3-dihydro-5-carboxanilido-6-methyl-1,4-oxathin-4-dioxide, phenylmercuric acetate, Polyram, 8-hydroxyquinoline sulfate, hydroxymercurinitrophenol and hydroxymercurichlorophenol mixture, sulfur, 5-ethoxy-3-trichloromethyl-1,2,4-thiadiazole, 1,2,4,5-tetrachloro-3-nitrobenzene, bis-(dimethylthiocarbamoyl) disulfide, 3,5,6-trichloro-o-anisic acid, triphenyltin hydroxide, 2,3-dihydro-5-carboxanilido-6-methyl-1,4-oxathiin, zinc ethylene bisdithiocarbamate, zinc dimethyl dithiocarbamate and lauryl isoquinolium bromide.

Some examples of insecticides and miticides include 0,0,0', 0'-tetramethyl 0,0'-thiodi-p-phenylene phosphorothioate, isopropyl 4,4'-dichloro-benzilate, 0-[2-chloro 1-(2,5-dichlorophenyl)-vinyl] 0,0-diethyl phosphorothioate, aldrin, allethrin, 0,0,0,0-tetrapropyl dithiopyrophosphate, 0,0-diethyl-S-[4-oxo-1,2,3-benzotriazine-3-(4H)-ylmethyl]-phosphorodithioate, 0,0-dimethyl-s-[4-oxo-1,2,3-benzotriazin-3-(4H)-ylmethyl]-phosphorodithioate, dimethyl phosphate of 3-hydroxy-N-methyl-cis-crotonamide, 2-isopropoxyphenyl N-methyl carbamate, benzene hexachloride (BHC), dimethyl phosphate of 3-hydroxy-N,N-dimethyl-cis-crotonamide, 2-sec-butyl-4,6-dinitrophenyl-3- methyl-2-butenoate, dimethyl 3-hydroxyglutaconate dimethyl phosphate (2,2,2-trichloro-1-hydroxyethyl) phosphorate ester of butyric acid, m-(1-methylbutyl) phenylmethyl carbamate, m(1-ethylpropyl) phenyl methyl carbamate, calcium cyanide, 1-naphthyl N-methylcarbate, 2,3-dihydro-2,2-dimethyl-7-benzofuranyl methyl carbamate, S-[(p-chlorophenylthio)methyl] 0,0-diethyl phosphorodithioate, m [[(dimethylamino)-methylene]-amino]phenyl methylcarbamate hydrochloride, chlordane, ethyl 4,4'-dichlorobenzilate, N,N-dimethyl-N'-(2-methyl-4-chlorophenyl)-formamidine, dimethyl phosphate of α-methylbenzyl 3-hydroxy-cis-crotonate, 0,0-diethyl-0-3-chloro-4-methyl-2-oxo-2H-1-benzopyran-7-ryl phosphorothioate, cyclic ethylene (diethoxyphosphinyl) dithiomido carbonate, 1,1-dichloro-2,2-bis(p-chlorophenyl)ethane, DDT (1,1,1-trichloro-2,2-bis (p-chlorophenyl)ethane, Demeton (mixture of 0,0-diethyl-0--[2-(ethylthio)ethyl] phosphorothioate and 0,0-diethyl-S-[2-(ethylthio) ethyl]-phosphorothioate 0,0-dimethyl-0-(2,2-dichlorovinyl phosphate (DDVP), 0,0-diethyl 0-(2-isopropyl-(o-methyl-4-pyrimidyl) phosphorothioate, 0-2-chloro-4-nitrophenyl 0,0-diethyl phosphorothioate, Dieldrin, 2-nitro-1,1-bis(p-chlorophenyl)butane, 2-nitro-1,1-bis-(p-chlorophenyl) propane, tetramethyl phosphorodia-midic fluoride, 2,4-dimethylbenzyl 2,2-dimethyl-3-(2-methyl propenyl) cyclopropanecarboxylate, 4,4'-dichloro-α-methylbenzhydrol, 4,6-dinitro-o-cyclohexylphenol, 2-secbutyl-4,6-dinitrophenyl isopropyl carbonate, 2,3-p-dioxane-dithiol-S,S-bis(0,0-diethyl phosphoro-dithioate), diphenylamine, 0,0-diethyl-S-[2-(ethylthio)-ethyl] phosphorodithioate, 0,0-diethyl-0-(3,5,6-trichloro-2-pyridyl)phosphorothioate, 0-ethyl-S-phenyl-ethylphosphonodithioate 6,7,8,9,10,10-hexachloro-1,5,5a,6,9,9a-hexahydro-6,9-methano-2,4,3-benzodioxathiepin-3-oxide, Endrin, 0-ethyl-0-p-nitrophenyl phenylphosphonothioate, 2,3-quinoxaline-dithiol cyclic trithiocarbamate, 0,0,0', 0'-tetraethyl S,S'-methylene bisphosphorodithioate, 0,0-dimethyl-0-[(4-methylthio)-m-tolyl]-phosphorothioate, 2-chloro-1-(2,4,5-trichlorophenyl) vinyl dimethyl phosphate, 2,4-dichlorophenyl ester of benzene sulfonic acid, Heptachlor, hydroxymercurichlorophenol, N-(mercaptomethyl) phthalimide S-(0,0-dimethyl phosphorodithioate), 2-(1-methylheptyl) 4,6-dinitrophenyl crotonate, decachlorooctahydro-1,3,4-metheno-2H-cyclobuta [pentalen-2-one, 2,3,5-trimethylphenyl carbamate, 3,4,5-trimethylphenyl carbamate, dibasic lead arsenate, β-butoxy-β'-thiocyanodiethyl ether, 1,2,3,4,5,6-hexachlorocyclohexane gamma isomers 5,6-dichloro-2-trifluoromethylbenzimidazole-1-carboxylate, 0,0-dimethyl phosphoro-dithioate of diethyl mercaptosuccinate, 4-(dimethylamino)-m-tolyl methylcarbamate, 0,0-diethyl-S-(N-ethoxycarbonyl)-N-methyl-carbamoylmethyl) phosphorothiolothionate, S-(4,6-diamino-s-triazin-2-ylmethyl) 0,0-dimethyl phosphorodithioate, 4-(methylthio)-3,5-tylylmethyl-carbamate, S-methyl-N-[(methylcarbamoyl)-oxy] thioacetamidate, 2,2-bis(p-methoxyphenyl-1,1,1-trichloroethane (Methoxychlor), bromomethane, o-[2-(ethylthio)ethyl] 0,0-dimethyl phosphorothioate (Meta Systox), 0,0-dimethyl-0-p-nitrophenyl phosphorothioate, S-[[(p-chlorophenyl)thio]methyl] 0,0-dimethyl phosphorodithioate, 3-(p-bromophenyl)-1-methoxy-1-methylurea, 2-carbomethoxy-1-methylvinyl dimethyl phosphate (α-isomer), 4-benzothienyl-N-methyl carbamate, O,S-dimethyl phosphor-amidi-thioate, 1,2-dibromo-2,2-dichloroethyl dimethyl phosphate, naphthalene, 2,2-dimethyl-3-(2-methylpropenyl) cyclopropanecarboxylic ester of N-(hydroxymethyl)-1-cyclohexene-1,2-dicarboximide, nicotine (3-(1-methyl-2-pyrrolidyl)pyridine), o-dichlorobenzene, p-chlorophenyl-p-chlorobenzenesulfonate, p-dichlorobenzene, 0,0-diethyl-0-p-nitro-phenyl phosphorothioate (Parathion), copper meta-arsenite copper acetate complex (Paris green), decachlorobis (2,4-cyclopentadiene-1-yl), 1,1-dichloro-2,2-bis(p-ethylphenyl)ethane, dibenzo 1,4-thiazine, 0,0-diethyl S-(ethylthio)-methyl phosphorodithioate, 2-chloro-2-diethylcarbamoyl-1-methylvinyl dimethyl phosphate, Piperonyl buoxide, 0-ethyl S,S-dipropyl phosphorodithioate, pyrethrins, 0,0-dimethyl-0-(2,4,5-trichlorophenyl) phosphorothioate, retenone, 4-t-butyl-2-chlorophenyl 0-methyl methylphosphoroamidate, ryanodine, sabadilla, (5-benzyl-5-furyl) methyl-2,2-dimethyl-3-(2-methyl-propenyl)-cyclopropanecarboxylate, octamethylpyrophosphoramide, sodium fluoride, 6(and 2)-chloro-3,4-xylymethylcarhbamate, polychlorinated (66% Cl) terpene, p-chlorophenyl phenyl sulfone, 0,0-dimethyl 0-(4-nitro-m-tolyl)-phosphorothioate, 2-methyl-2-(methylthio) propionaldehyde, O-methylcarbamoyl) oxime, tetraethyl pyrophosphate, 4-chlorophenyl 2,4,5-trichlorophenyl sulfone, isobornyl thiocyanoacetate, chlorinated (67–69%) camphene, 0,0-dimethyl (2,2,2-trichloro-1-hydroxyethyl) phosphonate and 0,0-dimethyl-O-(2-pyrozinyl) phosphorothioate.

Illustrative of nematocides are chloropicrin (trichloronitromethane), 0,0-diethyl 0[p-methylsulfinyl)-phenyl] phosphorothioate, 1,2-dibromo-3-chloropropane, D-D (mixture of 1,3-dichloropropene, 3,3-dichloropropene, 1,2-dichloropropane and 2,3-dichloropropene), 1,2-dibromoethane, 0-2, 4-dichlorophenyl 0,0-diethyl phosphorothioate, 3-bromo-1-propyne and tetrachlorothiophene.

Examples of some defoliants include arsenic acid, dimethyl arsinic acid, calcium cyanimide, S,S,S-tributyl phosphorotrithioate, 4,6-nitrophenol-0-sec. butyl-phenol, 6,7-dihydrodipyrido [1,1', 2,2'] pyrazinedium salts, S,S,S-tributyl phosphorotrithioite and magnesium chlorate.

The amount of pesticide employed in the pesticidal compositions of the present invention can vary greatly and is primarily dependent upon the effectiveness of the particular pesticide, and the desired effect. Accordingly, there is not real upper critical limitation nor lower critical limitation upon the amount of pesticide. The particular quantity of a pesticide to be employed in the present invention can readily be determined by those skilled in the art once they are aware of the present invention.

The substance employed according to the present invention which binds the pesticidal material to prevent immediate release and to provide for sustained release of the pesticidal material is a biological binding agent. The biological binding agents contain bonding sites which are complementary to bonding sites of the pesticide. That is, the biological binding agent contains bonding sites which interact with bonding sites present on the pesticide to bind or hold the pesticide. The complementary bonding sites of the pesticide and biological binding agent are of the type which are capable of providing for a sustained release of the pesticide of the desired dosage, and in particular provide an attractive face or bridge between the pesticide and biological binding agent so that the biological binding agent holds the pesticide as opposed to merely acting as a physical barrier such as an encapsulating layer for the pesticide. Included among the bonds employed according to this invention are ionic bonds, hydrogen bonds and hydrophobic bonds including van der Waal's forces. Examples of some pesticide-biological binding agent systems containing such complementary sites include the pesticide containing cations and the biological binding agent containing anions; the pesticide containing anions and the biological binding agent containing cations; both the pesticide and the biological binding agent are hydrophobic and the pesticide and biological binding agent containing polar moieties; and both the pesticide and the biological binding agent being hydrophobic or containing hydrophobic sites. The degree to which a particular pesticide is bound can be manipulated by selection of the biological binding agent and, in some instances, by the conditions of adding the pesticide and biological binding agent. The degree of bonding will in turn affect the release characteristics of the pesticide.

It is understood that the biological binding agents suitable from the present invention include both natural and synthetic biological substances; conjugates thereof; and derivatives including polymers thereof. Illustrative of derivatives are crosslinked biological materials such as dextrans crosslinked with epichlorohydrin, methylene bisacrylamide, cyanuric chloride, divinyl sulfone, bis epoxides (i.e. methylene bis epoxide), and bis aldehydes (i.e. terephthaldehyde); pharmacologically acceptable salts such as succinate, hydrochloride, phthalate, hydrobromide, sulfate, phosphate, nitrate, borate, acetate, maleate, tartrate, and the like; esters; ethers; amides; and the like. The biological binding agents employed according to the present invention have molecular weights of at least about 300 and usually at least about 10,000. The molecular weight of the biological binding agent should be higher than the pesticidal material bound thereto.

Exemplary of suitable biological binding agents include proteins, peptides, nucleic acids, carbohydrates, lipids, conjugates thereof and mixtures thereof.

The proteins which can be employed in the present invention can be simple proteins which contain only amino acids or can be conjugated proteins which contain amino acids plus other substances such as nucleic acids, carbohydrates, lipids, and the like. Included among the proteins which can be employed in the present invention are nucleoprotein, glycoprotein and phosphoproteins. Generally the proteins have molecular weights from about 6,000 to about 4,000,000. Preferably the molecular weight of the proteins is between about 10,000 and about 100,000. Some examples of proteins include albumins such as ovalbumin, and bovine or human serumalbumin; myoglobin; 3-lactoglobulin; hemoglobin; rennin; papain; prolamines such as zein; glutelins such as gluten; scleroproteins such as collagen, gelatin, elastins and keratins; protamines; histones; and phosphoproteins such as casein and vitellin. Other examples of protein-like biological binders include polymers of biological amino acids such as arginine, glutamic acid, asparatic acid, lysine, phenylalanine, tryptophan and the like.

Another group of biological binding agents for the pesticidal material are the carbohydrates including the polysaccharides. Generally the carbohydrates have molecular weights from about 1,000 to about 400 million and preferably from about 1,000 to about 100,000. Some examples of suitable carbohydrates include glycogen, cellulose, pentosans and hexosans, such as araban, xylans, dextrans and mannan; pectins, alginic acid, Chitin, inulin, agar, hyaluronic acid, ovomucoid heparin and chondroitin sulfate.

Another group of suitable biological binding agents for the pesticidal materials are the lipids including the phospholipids, glycolipids and proteolipids. Some specific examples of suitable lipids are lecithins, cephalins, sphinogomyelins, and cardiolipins. Preferably the fatty acid portions of lecithins, cephalins and sphinogomyelins are fatty acids containing about 12 to about 22 carbon atoms. The proteolipids generally have molecular weights from about 6,000 to about 4,000,000; and preferably from about 10,000 to about 100,000 whereas, the phosph lipids generally have molecular weights from about 500 to about 1500. The molecular weight of the glycolipids is usually from about 1,000 to about 400,000,000 and preferably from about 1,000 to about 100,000.

The nucleic acids include ribonucleic acids and deoxyribonucleic acids; and generally have molecular weights of at least about 1,000 and preferably about 10,000 to about 100,000.

The peptides include polypeptides and have molecular weights generally from about 500 to about 6,000.

The other essential constituent of the pesticidal compositions of the present invention is the water-insoluble but water-swellable hydrophilic polymer.

The water-insoluble but water-swellable polymers are obtained from a hydrophilic monomer and a crosslinking agent. Generally the crosslinking agent is present in an amount from about 0.05 to about 60% by weight, and preferably from about 0.1 to about 40% by weight. Some suitable examples of hydrophilic monomers include hydroxy lower alkyl acrylates or methacrylates, or hydroxy lower alkoxy lower alkyl acrylates or methacrylates, such as 2-hydroxy ethyl acrylate, 2-hydroxy ethyl methacrylate, diethylene glycol monoacrylate, diethylene glycol monomethacrylate, 2-hydroxy propyl acrylate, 2-hydroxy propyl methacrylate, 3-hydroxy propyl acrylate, 3-hydroxy propyl methacrylate, and dipropylene glycol monomethacrylate. Other suitable hydrophilic monomers include the heterocyclic polymerizable compounds containing a carbonyl functionality adjacent to the nitrogen in the heterocyclic ring such as the N-vinyl lactams, N-vinyl imidazolidones, N-vinyl succinimide, N-vinyl diglycolylimide, N-vinyl glutarimide, N-vinyl-3-morpholinone, N-vinyl-5-methyl-3-morpholinone. Usually the heterocyclic compounds contain from about 3 to 6 carbon atoms in the ring. Examples of some contemplated N-vinyl lactams include N-vinyl-2-pyrrolidone, N-vinyl-2-piperiodone, and N-vinyl-e-caprolactam.

Illustrative of some crosslinking agents are ethylene glycol diacrylate, ethylene glycol dimethacrylate, 1,2-butylene dimethacrylate, 1,3-butylene dimethacrylate, 1,4-butylene dimethacrylate, propylene glycol diacrylate, propylene glycol dimethacrylate, diethylene glycol dimethacrylate, dipropylene glycol dimethacrylate, diethylene glycol diacrylate, dipropylene glycol diacrylate, tetraethylene glycol dimethacrylate, glycidyl acrylate, glycidyl crotonate, divinyl benzene, divinyl toluene, diallyl tartrate, allyl pyruvate, allyl maleate, divinyl tartrate, triallyl melamine, N,N'-methylene bisacrylamide, glycerine trimethacrylate, diallyl maleate, divinyl ether, diallyl monoethylene glycol citrate, ethylene glycol vinyl allyl citrate, allyl vinyl maleate, diallyl itaconate, ethylene glycol diester of itaconic acid, divinyl sulfone, hexahydro-1,3,5-triacryltriazine, triallyl phosphite, diallyl ester of benzene phosphonic acid, polyester of maleic anhydride with triethylene glycol, polyallyl glucose, such as triallyl glucose, polyallyl sucrose, such as pentaallyl sucrose, sucrose diacrylate, glucose dimethacrylate, pentaerythritol tetraacrylate, sorbitol dimethacrylate, diallyl aconitate, divinyl citraconate, diallyl fumarate, and glycidyl methacrylate.

The preferred crosslinking agents include divinyl benzene, glycidyl acrylate, glycidyl methacrylate, and glycidyl crotonate. Some examples of suitable polymers which include glycidyl methacrylate, glycidyl acrylate, and/or glycidyl crotonate as the crosslinking agent are disclosed in U.S. patent applications Ser. Nos. 186,821; 186,822; and 187,131; all filed on Oct. 5, 1971, the entire disclosures of which are incorporated herein by reference. Illustrative of such polymers which include glycidyl acrylate, glycidyl methacrylate and/or glycidyl crotonate as a crosslinking agent are as follows:

I. Water insoluble but water swellable copolymer of a monomer mixture of:

A. a heterocyclic polymerizable compound containing a carbonyl functionality adjacent to the nitrogen in the heterocyclic ring, and being selected from the group consisting of N-vinyl lactams, N-vinyl imidazolidone, N-vinyl succinimide, N-vinyl diglycolyimide, N-vinyl glutarimide, N-vinyl-3-morpholinone, N-vinyl-5-methyl-3-morpholinone, and mixtures thereof; and preferably N-vinyl-2-pyrrolidone;

B. glycidyl methacrylate, and/or glycidyl acrylate, and/or glycidyl crotonate; and wherein the monomer mixture contains from about 40 to about 75% and preferably from 50 to about 65% by weight of the heterocyclic polymerizable compound, and from about 25 to about 60% and preferably from about 35 to about 50% by weight of the glycidyl ester based upon the total weight of (A) and (B) in the monomer mixture.

II. Water-insoluble but water-swellable copolymer of a monomer mixture of:

A. heterocyclic polymerizable compound containing a carbonyl functionality adjacent to the nitrogen in the heterocyclic ring and being selected from the group consisting of N-vinyl lactams, N-vinyl imidazolidone, N-vinyl succinimide, N-vinyl diglycolylimide, N-vinyl glutarimide, N-vinyl-3-morpholinone, N-vinyl-5-methyl-3-morpholinone, and mixtures thereof; and preferably being N-vinyl pyrrolidone.

B. monoethylenically unsaturated esters selected from the group consisting of alkyl acrylates, alkyl methacrylates, vinyl esters of saturated monocarboxylic acids of up to 22 carbon atoms, and mixtures thereof, wherein the alkyl group of said methacrylate or acrylate contains from 1 to 22 carbon atoms; and C. glycidyl esters selected from the group consisting of glycidyl methacrylate, glycidyl acrylate, glycidyl crotonate, and mixtures thereof; and wherein the monomer mixture contains from about 50 to about 90% by weight of (A), from about 5 to about 40% by weight of (B) and from about 0.5 to about 30% by weight of (C) based upon the total weight of (A), (B), and (C) in the monomer mixture.

The monomer mixture preferably contains from about 60 to about 80% by weight of (A), from about 25 to about 35% by weight of (A), and from about 2.5 to about 15% by weight of (C) based upon the total weight of (A), (B), and (C) in the monomer mixture, and most preferably contains from about 60 to about 70% by weight of (A), from about 25 to about 30% by weight of (B), and from about 4 to about 12% by weight of (C) based upon the total weight of (A), (B), and (C) in the monomer mixture.

III. Bulk polymerized water-insoluble but water-swellable copolymer of a monomer mixture of:

A. a polymerizable monoester of acrylic acid and/or methacrylic acid and a polyhydric alcohol, such as hydroxyethl methacrylate, hydroxyethyl acrylate, hydroxypropyl methacrylate, and hydroxypropyl acrylate; and B. glycidyl acrylate and/or glycidyl methacrylate and/or glycidyl crotonate; and wherein the monomer mixture contains based upon the total weight of the polymerizable monoester and the glycidyl ester from 60 to 99.75% and preferably from about 85 to about 97.5% of the polymerizable monoester and from 0.25 to 40% and preferably from about 2.5 to about 15% of the glycidyl ester.

Another specific group of polymers include water-insoluble but water-swellable copolymers of a monomer mixture of:

A. a polymerizable monoester of acrylic and/or methacrylic acid and a polyhydric alcohol such as hydroxyethyl methacrylate, hydroxypropyl methacrylate, and hydroxypropyl acrylate; and B. a crosslinking agent such as divinyl benzene, divinyl toluene, or a polymerizable diester of acrylic and/or methacrylic acid and a polyhydric alcohol such as ethylene glycol diacrylate, ethylene glycol dimethacrylate, 1,2-butylene dimethacrylate, 1,3-butylene dimethacrylate, 1,4-butylene dimethacrylate, diethylene glycol dimethacrylate, dipropylene glycol dimethacrylate, diethylene glycol diacrylate, dipropylene glycol diacrylate, tetraethylene glycol dimethacrylate, and tetraethylene gylcol diacrylate;

wherein the monomer mixture contains based upon the total weight of the polymerizable monoester and crosslinking agent from about 80% to about 99.95% and preferably from about 90% to about 99.9% by weight of the monoester and from about 0.05 to about 20% and preferably from about 0.1 to about 10% by weight of the crosslinking agent.

Illustrative of other polymers include water-insoluble but water-swellable copolymers of a monomer mixture of:

A. a heterocyclic polymerizable compound containing a carbonyl functionality adjacent to the nitrogen in the heterocyclic ring, and being selected from the group consisting of N-vinyl lactams, N-vinyl imidazolidone, N-vinyl succinimide, N-vinyl diglycolylimide, N-vinyl glutarimide, N-vinyl-3-morpholinone, N-vinyl-5-methyl-3-morpholinone, and mixtures thereof; and preferably N-vinyl-2-pyrrolidone;

B. monoethylenically unsaturated esters selected from the group consisting of alkyl acrylates, alkyl methacrylates, vinyl esters of saturated monocarboxylic acids of up to 22 carbon atoms, and mixtures thereof, wherein the alkyl group of said methacrylate or acrylate contains from 1 to 22 carbon atoms; and C. a crosslinking agent such as divinyl benzene, divinyl toluene, or a polymerizable diester of acrylic and/or methacrylic acid and a polyhydric alcohol such as ethylene glycol diacrylate, ethylene glycol dimethacrylate, 1,2-butylene dimethacrylate, 1,3-butylene dimethacrylate, 1,4-butylene dimethacrylate, diethylene glycol dimethacrylate, dipropylene glycol dimethacrylate, diethylene glycol diacrylate, dipropylene glycol diacrylate, tetraethylene glycol dimethacrylate, and tetraethylene glycol diacrylate;
wherein the monomer mixture contains based upon the total weight of heterocyclic polymerizable compound, unsaturated ester, and crosslinking agent, from about 90 to about 45% by weight and preferably from about 80 to about 55% by weight of the heterocyclic polymerizable compound, from about 5 to about 50% by weight and preferably from about 15 to about 45% by weight of the unsaturated ester; and from about 0.5% to about 15% by weight and preferably from about 1% to about 10% by weight of the crosslinking agent.

Generally the pesticide is employed in amounts of about 0.1 to about 50% and preferably from about 0.5 to about 20% by weight based on the total weight of the pesticide, biological binding agent, and the water-insoluble but water-swellable hydrophilic polymer. The amount of biological binding agent for the pesticide must be sufficient to adequately bond the pesticide to provide a sustained release of the pesticide in the desired dosage amount, and is generally from about 1 to about 80% by weight and preferably from about 20 to about 60% by weight based upon the total weight of pesticide, biological binding agent, and water-swellable hydrophilic polymer. The water-insoluble but water-swellable hydrophilic polymer is generally employed in amount of at least about 10% and preferably about 35 to about 60% by weight based upon the total weight of pesticide, biological binding agent, and hydrophilic polymer.

In addition, the pesticidal compositions of the present invention can include such other materials as suspending aids for the pesticide or biological binder including Cab-O-Sil and bentone; plasticizers and inert fillers.

Moreover, the pesticidal compositions of the present invention can be further encapsulated by another polymeric or other film-forming substance according to particular applications of the pesticidal composition. Such auxiliary encapsulating layers can be soluble or insoluble in aqueous medium, the solubility or swelling being dependent or independent of pH and/or ionic strength.

The pesticidal compositions of the present invention can be prepared by admixing a mixture of monomeric materials which are polymerizable to the water-insoluble but water-swellable polymer and the biological binder for the pesticide. The resulting composition is then polmerized to provide a matrix of a water-insoluble but water-swellable hydrophilic polymer retaining or holding the biological binder for the pesticide. After the polymerization, the pesticide is contacted with the resulting composition in such a manner as to be sorbed into the matrix of the water-swellable polymer and to be bound to the biological binding agent to thereby provide a sustained release pesticidal composition. In particular, the combination of the biological binding agent and the matrix of water-insoluble polymer can be impregnated with the pesticide by immersion in a bath such as an aqueous bath of the pesticide to cause the pesticide to diffuse into the matrix and be bound by the biological binding agent.

In some instances, it may be desirable to employ a liquid diluent along with the biological binding agent (i.e., an alcohol) to facilitate mixing with the monomers. Generally the pesticide is contacted with the biological binder for at least about 15 minutes to cause bonding. Of course, this can vary greatly depending upon the relative amount of the ingredients including the amount of matrix material, and the affinity of the pesticide and biological binder for each other.

Moreover, the compositions of the present invention can be prepared by initially contacting the pesticide with the biological binding agent therefor to achieve bonding between the pesticide and the biological binding agent. Then, either the resulting composition can be admixed with a monomer mixture polymerizable to the water-insoluble but water-swellable polymer followed by polymerization or can be encapsulated or coated with an already polymerized water-insoluble polymer. In either case, the resultant product is a matrix of the water-insoluble but water-swellable polymer containing the biological binding agent having the pesticide bound to the biological binding agent.

The water-swellable polymers employed in the present invention generally can be prepared by employing bulk polymerizaton techniques. The term "bulk polymerization" as used herein includes those polymerizations carried out in the absence of a solvent or dispersing liquid as well as those polymerizations carried out in the presence of water or water-soluble or polymer-soluble liquid swelling agents in such amounts as not to significantly alter the nature of the polymerization process.

The polymerization catalyst employed can be any of the catalysts which are suitable in polymerizing compounds containing ethylenic unsaturation and preferably are the free radical catalysts. Of particular interest are the peroxide catalysts. Some examples of suitable peroxide catalysts include hydrogen peroxide, benzoyl peroxide, tert-butyl peroctoate, phthalic peroxide, succinic peroxide, benzoyl acetic peroxide, tert-butyl peroxy pivalate, coconut oil acid peroxide, lauric peroxide, stearic peroxide, oleic peroxide, tert-butyl hydroperoxide, tetraline hydroperoxide, tert-butyl diperphthalate, cumene hydroperoxide, tert-butyl perbenzoate, acetyl peroxide, 2,4-dichlorobenzoyl peroxide, urea peroxide, caprylyl peroxide, p-chlorobenzoyl peroxide, ditert-butyl peroxide, 2,2-bis(tert-butyl peroxy)-butane, hydroxyheptyl peroxide, and the diperoxide of benzaldehyde; alkylperoxycarbonates such as diisobutylperoxy bicarbonate, di-secondary butyl peroxy bicarbonate, and tert-butyl peroxyisopropylcarbonate, and the like. The preferred catalyst is one which is effective at moderately low temperatures such as at about 30°–90° C.

When the crosslinking agent is a glycidyl compound such as glycidyl methacrylate, it may be desirable that the catalyst in addition to containing the free radical polymerization catalyst may include a material which accelerates polymerization primarily by opening of the epoxide group of the glycidyl ester. Such catalysts include p-toluene sulphonic acid, sulfuric acid, phosphoric acid, aluminum chloride, stannic chloride, ferric chloride, boron trifluoride, boron trifluoride-ethyl ether complex, and iodine. Also, when the crosslinking agent includes a glycidyl compound, it may be desirable to employ a multistage polymerization process. For instance, the polymerization can initially be conducted until substantially all of the unsaturated groups have polymerized, and then can be conducted to effect polymerization through the breaking of the oxirane group of the glycidyl ester and condensation.

The amount of catalyst employed depends upon the type of catalyst system used and is generally from about 0.01 to about 10 parts by weight per 100 parts of the monomer mixture, and preferably is from about 0.1 to about 1 part by weight per 100 parts of the monomer mixture.

The polymerization is generally carried out at temperatures from about room temperature to about 150° C. It is generally preferred to initiate the polymerization at relatively low temperatures such as from about 35° to about 85° C and then to increase the temperature to about 90° to about 150° C as the reaction proceeds and preferably after most of the reaction has been completed. The most preferred initial temperature range of polymerization is between about 30° and 90° C.

Usually the polymerization is conducted under autogenous pressure in a closed reaction vessel. However, any suitable means to prevent significant evaporation of any of the monomers can be employed.

Generally, the polymerization is completed in about ½ to about 12 hours and preferably is completed in about 4 to about 6 hours. It is understood, of course, that the time and temperature are inversely related. That is, temperatures employed at the upper end of the temperature range will provide polymerization processes which can be completed near the lower end of the time range.

In addition, it may be desirable for the copolymers obtained from such polymerizations to be post cured at temperatures somewhat higher than those initially employed in the polymerization. Usually the temperatures employed in the post cure will range from about 90° to about 150° C. Two hours is usually more than sufficient for such a post curing operation. Preferably the post cure is completed in 2 to 4 hours.

Upon application to the desired environment by the desired mode, the pesticidal compositions of the present invention provide sustained release of the pesticide by allowing it to diffuse through pores of the water-insoluble but water-swellable polymeric matrix upon contact with a liquid such as an aqueous solution. In addition, the biological binding agent is retained by the matrix of the water-insoluble but swellable polymer during the treatment period.

The present invention makes it possible to obtain a sustained release pesticidal composition employing a biological material as the binding agent for the pesticide, which would not be achieved without all of the essential components of this invention. For instance, the water-insoluble but water-swellable polymeric matrix protects the biological binding agent so as to at least significantly retard and in many cases prevent deterioration of the biological binding agent when the composition is in use. For instance, the matrix protects biological binding agents employed in the present invention from being dissolved during the treatment period when the pesticidal composition is in contact with or other liquids. Dissolution of the biological binding agent, of course, would defeat the main purpose of the present invention of providing a sustained release preparation. In addition, the present invention makes it possible to better control the sustained release characteristics of the pesticide. For instance, the biological binding agent can be selected for a particular pesticide to provide a rate of release desired for a particular application of the preparation. This control or tailoring of the rate of release is achieved since the biological binding agent actually binds the pharmacological material in the manner previously described and since the strength of the bond between a particular biological binding agent and different pesticides can vary. This effect is quite different from systems wherein the material used to regulate the release of the pesticide merely acts as a physical barrier and does not bind the pesticide according to the present invention. For instance, a particular physical barrier would release all pesticides of similar molecular size at substantially the same rate. In addition, the matrix and amount thereof can be selected so as to slow down the rate of release in addition to the protection functions discussed above.

Moreover, the present invention makes it possible to employ lesser relative quantities of non-biological materials based upon the amount of pesticide than generally used in preparing sustained release pesticidal compositions.

The following non-limiting examples are provided to further illustrate the present invention. All parts are by weight unless the contrary is stated.

EXAMPLE 1

A zein-containing composition is prepared by admixing about 8 parts of zein, about 15.5 parts of methanol and about 77 parts of a polymerizable composition containing about 58.4% by weight of N-vinyl-2-pyrrolidone, 40.0% by weight of methyl methacrylate, 1% by weight of divinylbenzene and 0.6% of t-butyl peroxypivalate. The mixture is heated to 40° C for about 12 hours under a nitrogen atmosphere to effect polymerization. The composition is then post cured by heating at 100° C for about 2 hours at atmospheric pressure.

About 80 parts of the resulting polymer composition are soaked for about 12 hours at ambient temperature in about 5000 parts of a solution of methanol containing about 100 mg of para-dichlorobenzene. The above composition is introduced into a beaker containing 20 milliliters of isotonic saline solution (0.9% NaCl) and the beaker is shaken at a constant temperature of 37° C in a thermostatic water bath shaker. The concentration of eluted para-dichlorobenzene is determined with a Beckman DB-GT spectrophotometer using the maximum absorption of p-dichlorobenzene at 280 nanometers.

Elution rates are checked at ½ hour intervals and fresh isotonic saline is employed after each reading.

The composition provides for sustained release of the p-dichlorobenzene over a prolonged period of time.

EXAMPLE 2

Example 1 is repeated except that the zeinpolymer composition is soaked for about 12 hours at ambient temperature in about 5000 parts of an isotonic saline solution (0.9% NaCl) containing about 100 mg of salicyclic acid. The concentration of eluted salicylic acid is determined with a Beckman DB-GT spectrophotometer using the maximum absorption of salicylic acid at 296 nanometers.

The composition provides for sustained release of the salicyclic acid over a prolonged period of time.

EXAMPLE 3

Example 1 is repeated except that the zeinpolymer composition is soaked for about 12 hours at ambient temperature in about 5000 parts of an isotonic saline solution (0.9% NaCl) containing about 100 mg of cetylpyridinium chloride. The concentration of eluted cetylpyridinium is determined with a Beckman DB-GT spectrophotometer using the maximum absorption of cetylpyridinium chloride.

The composition provides for sustained release of the cetylpyridinium over a prolonged period of time.

What is claimed is:

1. A sustained release pesticidal composition comprising:
   A. a quaternary ammonium bactericide in an amount at least sufficient for the total dosage during a treatment period;
   B. a biological binding agent for said pesticide; said biological binding agent being zein and containing bonding sites complementary to bonding sites of said bactericide in an amount effective to bind the bactericide and to provide for the sustained release of said bactericide in the desired dosage amount;
   C. a matrix of a water-insoluble but water-swellable hydrophilic polymer, which holds said biological binding agent and which is a copolymer of a monomer mixture of N-vinyl-2-pyrrolidone, methyl methacrylate, and divinyl benzene wherein the monomer mixture contains based upon the total weight of N-vinyl-2-pyrrolidone, methyl methacrylate, and divinyl benzene, from about 90 to about 45% by weight of the N-vinyl-2-pyrrolidone, from about 5 to about 50% by weight of the methacrylate, and from about 0.5 to about 15% by weight of divinyl benzene;
   D. the molecular size or weight of the biological binding agent being sufficient to cause retention of said biological binding agent in said matrix and to prevent egress of said biological binding agent from said matrix during the treatment period.

2. The sustained release pesticidal composition of claim 1 wherein said bactericide is present in an amount from about 0.1 to about 50% by weight based upon the total weight of the bactericide, biological binding agent, and the water-insoluble but water-swellable hydrophilic polymer.

3. The sustained release pesticidal composition of claim 1 wherein said bactericide is present in an amount from about 0.5 to about 20% by weight based upon the total weight of the bactericide, biological binding agent, and the water-insoluble but water-swellable hydrophilic polymer.

4. The sustained release pesticidal composition of claim 1 wherein the biological binding agent is present in an amount from about 1 to about 80% by weight based upon the total weight of the bactericide, biological binding agent, and water-insoluble but water-swellable hydrophilic polymer.

5. The sustained release pesticidal composition of claim 1 wherein the biological binding agent is present in an amount from about 20 to about 60% by weight based upon the total weight of the bactericide, biological binding agent, and water-insoluble but water-swellable hydrophilic polymer.

6. The sustained release pesticidal compositon of claim 1 wherein said bactericide is cetylpyridinium chloride.

* * * * *